United States Patent [19]

Hochberg

[11] Patent Number: 4,465,676
[45] Date of Patent: Aug. 14, 1984

[54] 16α HALOGEN SUBSTITUTED 3,17β-DIHYDROXY STEROIDAL ESTROGENS

[75] Inventor: Richard B. Hochberg, West Englewood, N.J.

[73] Assignee: New England Nuclear Corporation, Boston, Mass.

[21] Appl. No.: 138,267

[22] Filed: Apr. 9, 1980

[51] Int. Cl.³ .............................................. A01N 45/00
[52] U.S. Cl. ................................... 424/238; 260/397.5; 422/61
[58] Field of Search ............... 260/397.4, 397.3, 397.5; 424/238

[56] References Cited
U.S. PATENT DOCUMENTS 2,855,413  10/1958  Mueller ........................ 260/397.5

OTHER PUBLICATIONS

Ghanadian et al., "International Journal of Applied Radiation and Isotopes", (1975), vol. 26, pp. 343-346.
Arunachalam et al., J. Biol. Chem. 254, (1979), pp. 5900-5905.

Primary Examiner—Elbert L. Roberts
Attorney, Agent, or Firm—Sewall P. Bronstein; George W. Neuner

[57] ABSTRACT

16α-Radiohalo-3,17β-dihydroxy steroidal estrogens and their radiolabelled analogs are described. These steroidal estrogens have high estrogen receptor activity and are prepared by halogen exchange with the corresponding 16β-bromo compound. The radiolabelled estrogens of this invention are useful in estrogen receptor assays, radioimmunoassays, in vivo imaging of tissue having estrogen receptor activity, and for therapeutic treatment of tumors having estrogen receptor activity.

18 Claims, 2 Drawing Figures

16α HALOGEN SUBSTITUTED 3,17β-DIHYDROXY STEROIDAL ESTROGENS

FIELD OF THE INVENTION

This invention relates to halogenated steroidal estrogen particularly to 16α halogen substituted 3,17β-dihydroxy steroidal estrogens where the halogen is radioactive, such as radioiodated 16α-iodoestra-1,3,5(10)-triene-3,17β-diol their method of preparation and methods for their use.

BACKGROUND OF THE INVENTION

It has been recognized that estradiol, i.e. estra-1,3,5(10)-triene-3,17β-diol, and certain analogs and derivatives thereof have estrogen receptor activity. In recent years, it has been postulated that radioiodinated estradiol might be useful for several diagnostic purposes including applications in estrogen receptor assay, radioassay of estrogens and in-vivo radioimaging of certain tumors and organs. As such estradiols and related compounds and particularly radioiodinated analogs thereof have received considerable investigation and publication in the literature. See, for example, Arunachalam et al., *J. Biol. Chem.*, 254, 5900–5 (1979); Tarle et al., *J. Lab. Comp. Radiopharm.* Vol. XV, pp. 665–671 (1978); Maysinger et al. *J. Chromatog.* 130, 129–138 to (1977); *J. Steroid Biochem.* 5, 749–756 (1974), Antar et al., Fed. Proc. 33 (3 Part 1), p. 267(1974); Thaleur et al., *Int. J. Appl. Rad. and Isotopes*, 27 585–588(1978) Kormai et al., *J. Nuclear Med.* 18, 360–366 (1977); Albert et al *J. Biol. Chem.* 177, 247–266 (1949); Ghanadian et al., *Int. J. App. Rad. and Isotopes* 26, 343–46 (1975); Katzenellenbogen et al., *Biochem.* 14, 1742–1750 (1975); and Korenman, *Steroids* 13, 163–177 (1969).

As stated In Katzenellenbogen et al., supra, if an estrogen derivative is to be used in an estrogen receptor assay or for in-vivo radioimaging techniques, it must fulfill three criteria: (1) the linkage of the iodine atom to the ligand must be chemically and metabolically stable; (2) the site of iodine substitution must be such that the derivative is still capable of binding with high affinity to the specific-estrogen binding proteins found in estrogen target tissues, and (3) the physicochemical properties of the derivative (polarity, etc.) must be such that it does not bind excessively to the low affinity, high capacity binding proteins found in serum and tissues. None of the radioiodinated estrogen derivatives studied to date appear to meet the above three requirements necessary for such applications. In addition to the three requirements outlined by Katzenellenbogen et al. above useful radioactive estrogen derivatives should also have high specific activity and be easy to make.

It has been recognized that aliphatic iodine compounds have a high susceptibility toward substitution and elimination reactions and, on the grounds, of chemical stability, it is preferred to have the iodine bonded to an aryl group. Although several compounds having aryl groups substituted with iodine have been made that appear to be metabolically stable, such compounds have shown either low or negligible estrogen receptor activity.

A radioiodinated estrogen analog meeting the three requirements set forth above is highly desired in the medical field.

The chemistry of C-16 halides of estrone methyl ester, including proof of structure, isomerization, interconversion and reduction, has been thoroughly discussed by Mueller et al., *J. Am. Chem. Soc.* 26, 2403–2413 (1961).

In 1969, Korenman, supra, reported on a study of comparative binding affinity of various estrogens and its relation to estrogenic potency. He concluded that no unitary criterion of relative estrogenic potency can be given. Katzenellenbogen et al., supra, reported that the estrogen receptor is relatively intolerant of bulk at A-ring positions 2 and 4 so that functionalization of these positions would not be consistent with high receptor binding.

Although tritium and carbon 14 remain the usual radioactive isotopes for labeling steroids, for the past several years attempts have been made to use other radioactive isotopes for this purpose. These isotopes include 18-fluorine and 75-selenium, but the commonest have been the radioactive isotopes of iodine. Arunachalam et al., supra, state that so far the results of these endeavors have not been very successful in part due to nonspecific labeling techniques, to loss of biologic activity following iodination, or to nonspecific binding of the iodinated molecule.

Arunachalam et al. undertook to evaluate the utility of iodoestradiol analogs made highly radioactive with iodine isotopes in (a) the non-invasive differentiation of estrogen-dependent from estrogen-independent breast tumors, (b) spread of metastases containing estrogen receptors, and (C) potential application in therapeutic irradiation of target tissues. The model syntheses of a number of nonradioactive $^{127}$I-estrogen analogs are described. The analogs were tested for their ability to displace (compete with) [$^3$H]estradiol from receptor sites. The most active compounds, 16β-iodoestra-1,3,5(10)-triene-3-17β-diol and 6-iodoestra-1,3,5(10), 6-tetraene-3,17β-diol showed a relative binding affinity of 0.57 and 0.49, respectively. They prepared and evaluated 16α-iodo-3-hydroxyestra-1,3,5(10)-triene-17-one but concluded the introduction of the iodine group at the 16β position does not diminish binding to the same extent as 16α substitution and stated that this finding was consistant with a report on the difference in binding between estriol and epiestriol. Further, Counsell et al., in *Steroid Hormone Action and Cancer*, Menon and Reel, Eds., Plenum, New York (1976) at p. 107 indicate that the 16α substituted estrone would not be useful. This is probably because the estrone is metabolically and chemically unstable.

Upon considering these disclosures, one skilled in the art would not contemplate that iodo substitution at the 2,4, or 16α position would fulfill the three requirements set forth above.

SUMMARY OF THE INVENTION

The present invention provides 16α radio halogen substituted 3,17β dihydroxy steroidal estrogens, such as estradiols. These steroidal estrogens that are radiohalogenated at the 16α position have high affinity to estrogen receptors, and are chemically and metabolically stable. Preferably the radiohalogenated steroidal estrogens of the invention have a specific activity of at least about 1000 Ci/mmol.

The 16α halogenated steroidal estrogens of the invention are preferably made by halogen exchange reaction from corresponding 16β-bromo substituted steroidal estrogens using a high molar excess of the 16β-bromo steroidal estrogen. In the exchange reaction, the new halogen atom is substituted in the α position for the original bromine atom in the β position. The halogen atom being substituted can be cold or hot, i.e. radioactive. Preferred radiohalogens are radioiodides such as $^{123}I$, $^{125}I$, and $^{131}I$.

The 16α halogen steroidal estrogens of this invention which are radiolabelled at the 16α position can be used in estrogen receptor assays, in radioimmunoassays for steroidal estrogens for in-vivo localization of estrogen receptor-containing tissue, such as tumors, by radioimaging, and therapeutic treatment cancerous tissue containing estrogen receptors.

In this disclosure certain abbreviations are used as follows: "$E_2$" means estradiol (i.e., 1,3,5,(10)-triene-3,17β-diol); "I-$E_2$" means 16α-iodoestradiol (i.e. 16α-iodoestra-1,3,5,(10)-triene-3,17β-diol); "$^{125}I$-$E_2$" means $E_2$ radioiodinated with $^{125}I$ at the 16α position; and "$^3H$-$E_2$" means $E_2$ radiolabelled with tritium.

DETAILED DESCRIPTION OF THE INVENTION

Figure 1:
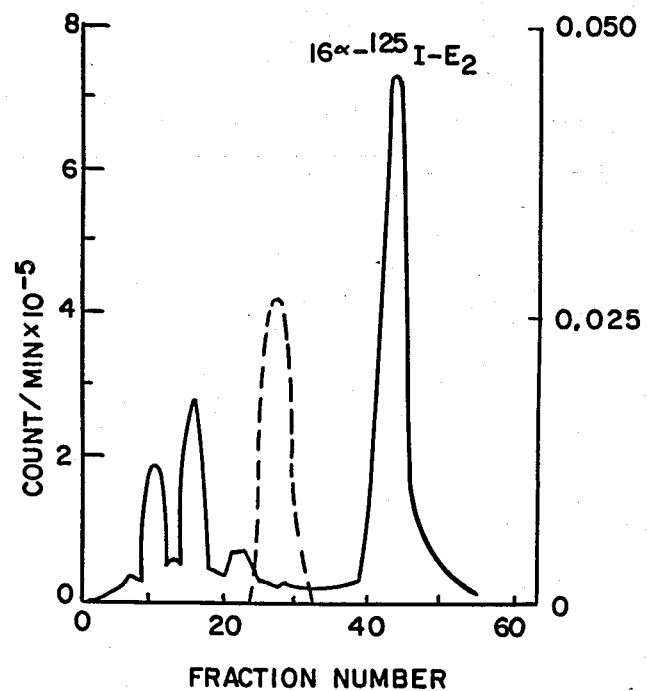
FIG. 1 is a graph illustrating the separation of $^{125}I$-$E_2$ from the reaction mixture.

In accord with the present invention 16α radio halogenated 3,17β-dihydroxy steroidal estrogens are provided. Preferably radioiodides are substituted at the 16α position however any radioactive halogen can be used depending upon the particular application. The invention will be described in detail with reference to the compound 16α-iodoestradiol (I-$E_2$). However, it will be appreciated by those skilled in the art that the methods and uses described herein apply similarly to any 3,17β-dihydroxy steroidal estrogen such as, for example, 17β-dihydro equilin and 17β-dihydro equilenin.

A description of I-$E_2$ and its radioiodide analogs has been published by, Richard B. Hochberg, Science 205, pp. 1138-40(1979) and by Hochberg and Rosner, Proc. Natl. Acad. Sci. USA, Vol 77, No. 1, pp. 328-332 (1980), which are hereby incorporated by reference. These estradiols have a high affinity to estrogen receptors, are highly specific for such receptors, and are chemically and metabolically stable. Preferably, the radio-labelled I-$E_2$ has a specific activity of 1000 Ci/mmol of I-$E_2$ or greater. From kinetic experiments and Scatchard analyses in rat uterine cytosol, the binding constant, $K_d$, of $^{125}I$ labeled estradiol, $^{125}I$-$E_2$ was found to be $2.7 \times 10^{-10}$ which is very close to that to tritiated estradiol, $^3HE_2$ ($K_d = 1.6 \times 10^{-10}$).

In accord with the invention, the 3,17β-dihydroxy steroidal estrogens having a halogen substituted at the 16α position can be made from the corresponding 16β-bromo steroidal estrogen by halogen exchange. The exchange reaction results in inversion at the 16 position. The 16β-bromo steroidal estrogen is made by known techniques. This inversion allows the desired 16α substituted product to be separated from the 16β-bromo starting material. Because both of the 16β-bromo starting material and the 16α-halogen substituted product have estrogen receptor activity it is important to remove the starting material to avoid an apparent low specific binding activity for the desired 16α-halogen substituted product.

Conventional halogen exchange reactions are generally conducted using a large molar excess in the ratio of halide to substrate to drive the reaction to completion. Such a large excess of halogen is not desirable in radiolabelling because of the desired activity. Thus, I have found that a large molar excess of the 16β-bromo substrate is required in order to obtain desire 16α-halogen substituted steroidal estrogens having high specific activity. As aforesaid the 16α compounds can be readily separated from the 16β-bromo starting material by chromatography yielding a pure 16α-halogen substituted product having high specific activity. By a large molar excess, for purposes herein, it is meant that the moles of the 16β-bromo estrogen are present in an amount at least about 10 times the number of moles of radiohalogen and preferably in an amount at least about 20 times the moles of radiohalogen and most preferably in an amount of about 30 times the moles of radiohalogen.

For example, 16α-iodoestradiol V can be prepared in accord with the following reaction scheme:

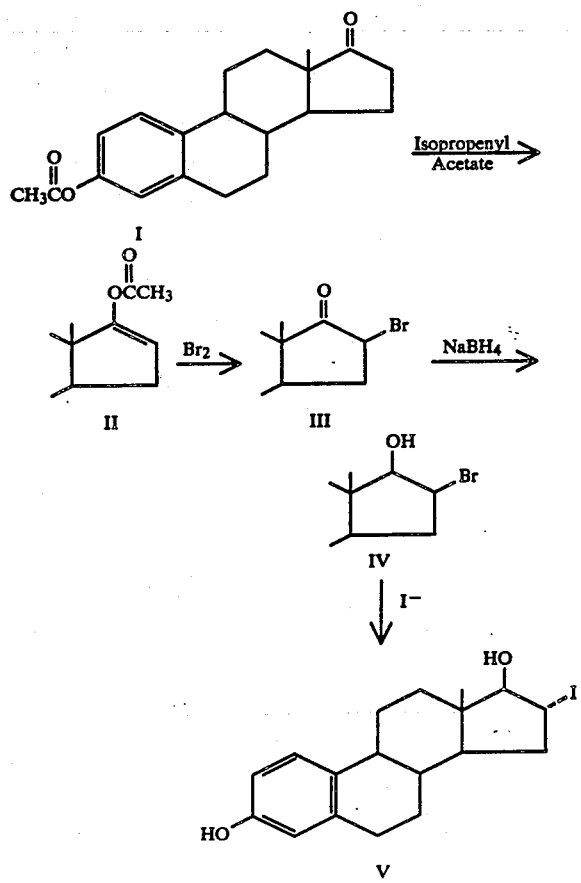

The 3-acetate-estrone I is acetylated to form the enoldiacetate of estrone II which is brominated at the 16 position and epimerized with LiBr to form 16β-bromo-17-estrone III. The major product of the bromination is 16α-bromoestrone which is inverted by epimerization to 16β-bromoestrone. The 16β-bromoestrone III is reduced with $NaBH_4$ to 16β-bromoestradiol IV. Exchange of the bromide for iodide causes further inversion to 16α-iodoestradiol V. Radioactive iodide alone or mixed with carrier, i.e. non-active iodide, can be used in the final inversion step to radiolabeled the end product. Any suitable isotope of iodine can be used depending upon the end use for the labelled compound. The isotopes, $^{123}I, ^{125}I$ and $^{131}I$, are preferred. Other halides can be used in the above reaction using conventional techniques for modifying the reaction scheme.

The specific binding of the $^{125}I$-labeled estradiol compared favorably with that of [$^3H$]estradiol, indicating that more sensitive assays than that obtainable with [$^3H$]estradiol could be performed with this high-specific activity tracer. In addition, $^{125}I$-labeled estradiol does not bind to the testosterone-estradiol binding globulin present in human plasma. This protein contaminates most human tissue preparations, complicating the detection of sex steroid receptors. The use of the $^{125}I$-labeled estradiol of this invention as a ligand in such assays will eliminate the "nonspecific" binding caused by this protein. Kinetic experiments and Scatchard analysis indicate that in rat uterine cytosol the binding constant, $K_d$ of $^{125}I$-labeled estradiol, is very close ($K_d = 2.7 \times 10^{-10}$) to that of [$^3H$]estradiol ($K_d = 1.6 \times 10^{-10}$).

The radiolabeled I-E$_2$ has a specific activity of at least 50 Ci/mmol. Preferably the specific activity is 1000 Ci/mmol or greater. As used herein, specific activity is determined by direct physical measurement of mass and radioactivity and confirmed by displacement in a receptor assay as illustrated in Example 8.

Radiolabeled I-E$_2$ is quite stable and shows little sign of decomposition after weeks of storage of 4° C.

Radiopharmaceutical preparations for in-vivo imaging in accord with my invention contain radiolabeled 16α-halogen substituted 3,17β-dihydroxy steroidal estrogen, in a pharmaceutically acceptable carrier. Any suitable pharmaceutically acceptable carrier may be used. For example, a physiological buffer solution is satisfactory. Other materials can be added to stabilize the solution, etc. as needed. The radiopharmaceutical preparations of this invention can be injected intravenously or lymphatically into higher animals depending upon the particular sites being visualized. The amount of radiolabeled estrogen injected depends upon upon the biological activity and the amount of labelling. The amount of injected estrogen can be determined by those skilled in the art using routine methods that depend upon various known considerations including, for example, the particular radionuclide used for labelling, the target tissue, the rate of clearance from the blood or lymphatic system, clearance from the most sensitive tissues, whole body clearance, etc. The acceptable ranges for administration of radiolabeled materials for various procedures are tabulated, for instance, in the Physician Desk Reference for Nuclear Medicine published by Medical Exonomics Co. A discussion of some of these considerations is given by Eckelman et al., *J. Nucl. Med.*, 20: 350-357 (1979), which is hereby incorporated by reference.

The radiopharmaceutical preparations of this invention containing radiolabelled I-E$_2$, when injected into rats, provide radioactivity concentrations at areas of estrogen receptor activity. The areas expressing estrogen receptor activity can then be visualized using radioscintigraphic imaging equipment. The advantage of having a radiolabelled material that localizes specifically in areas of estrogen-receptor activity will be readily appreciated by those skilled in the art. For instance, such radiopharmaceutical preparations can be used for the therapeutic treatment of tumors. When used for therepeutic treatment the radioactive estrogen must be present in a therapeutically effective tumor treating amount which is determined by those skilled in the art based on the aforementioned considerations and the desired therapeutic result.

In accord with the invention, radiolabelled 16α-halo-3,17β-dihydroxy steroidal estrogens are useful for estrogen receptor assays for determining the binding capacity of cytosol protein. The procedure used in the receptor assay is similar to that conventionally used when the receptor assay is conducted using $^3H$-E$_2$ as the radiolabelled tracer. The procedure is well known to those skilled in the art. An estrogen receptor assay kit according to the invention comprises a container having positive control derived from animal tissue, a container having negative control derived from animal tissue, and a container having radiohalogenated 16α-halo-3,17β-dihydroxy steroidal estrogen for use as a tracer. Preferably the kit contains six containers of tracer, each container having a different total radioactivity for conducting tests for a six point titration curve. Additionally the estrogen receptor assay kit can contain one or more of the following: a container of assay buffer (generally tris-HCl), a container of monothioglycerol, a container of diethylstilbestrol, a container of bovine serum albumin (usually 4%), and a container of charcoal suspension.

For example, an estrogen receptor kit using 16α-[$^{125}I$]iodoestra-1,3,5(10)-triene-3,17β-diol comprises:

---
1 bottle Tris-HCl buffer - 150 ml
1 vial Monothioglycerol - 1 ml
1 vial Diethylstilbestrol - 50 μg/ml, 1 ml (lyophilized)
2 vials Positive Control - 75 mg/vial (lyophilized)
2 vials Negative Control - 50 mg/vial (lyophilized)
1 vial 4% Bovine Serum Albumin Standard - 1 ml
1 Bottle Charcoal Suspension - 150 ml
6 vials $^{125}I$-E$_2$ Tracers
(containing appropriate total activities
of 3.6, 1.8, 0.8, 0.5, 0.3 and 0.2
μCi/vial respectively) - 4 ml/vial
---

In accord with this invention, radiolabelled 16α-halo-3,17β-dihydroxy steroidal estrogens are useful for radioimmunoassay (RIA) of estrogens in plasma or serum. The amount of, for instance, estrone (E$_1$) and estradiol (E$_2$) in plasma or serum can thus be determined using procedures well known to those skilled in art for RIA's using $^3H$-E$_2$ as a tracer. Sheep antiserum to the estrogen being assayed is prepared by conventional techniques. An RIA kit for the determination of estrogen levels in a sample in accord with this invention comprises a container of antiserum to the estrogen being assayed. A container of radiohalogenated 16α-halo-3,17β-dihydroxy steroidal estrogen that competes in a predetermined manner with the estrogen being assayed, and a container of estrogen standard for the estrogen being assayed. For convenience other components useful in the assay such as, for example, a container of assay buffer, a container of charcoal suspension, etc. can also be included in the RIA kit.

For example, a radioimmunoassay kit for assaying estrone and/or estradiol in accord with this invention using $^{125}I$-E$_2$ as the tracer comprises:

---
1 vial lyophilized Estrogen (E$_1$/E$_2$) Antiserum (Sheep)
1 vial $^{125}I$-E$_2$ Tracer - 1.5 μCi
1 vial Estradiol (E$_2$) Standard Solution - 100 ng/ml, 2 ml
1 vial Estrone (E$_1$) Standard Solution - 100 ng/ml, 2 ml
---

This kit is sufficient for assaying 100 Tubes.

Other advantages of the materials and methods of this invention will be apparent to those skilled in the art upon consideration of the following examples which are provided to further aid in the understanding and practice of my invention.

EXAMPLE 1

Preparation of 16β-Bromoestradiol

16α-Bromoestrone was prepared by bromination of the enol acetate of estrone and then epimerized with LiBr (as described by Fishman et al., *J. Org. Chem.* 23, 1190 (1958) and Mueller et al., supra, which are hereby incorporated by reference). The resulting mixture of 16α- and 16β-bromoestrone was reduced with NaBH$_4$. All four of the possible bromohydrins were isolated from the reaction mixture by chromatography on silica gel in 5 percent ethyl acetate in benzene. The second compound eluted from the column (60 percent of the reaction mixture) melted at 176° to 178° C., where-upon a new crystalline structure formed (melting point, 255° to 256° C.). It was identified as 16β-bromoestradiol by reaction with KOH to form estrone (cis-bromohydrin); epimerization with LiBr to form 16α-bromoestradiol (compared to an authentic sample); and its mass spectrum. 16α-Iodoestradiol (melting point, 190° to 191° C.) was synthesized from 16β-bromoestradiol by exchange with NaI. Its nuclear magnetic resonance (NMR) and mass spectra were consistent with the predicted structure.

EXAMPLE 2

16α-[$^{125}$I]iodoestradiol

A solution of 1 mCi of Na$^{125}$I (17 Ci,mg; New England Nuclear) in 3 μl of water, pH 8 to 10, was added to 100 μl of acetonitrile in a 300-μl tapered Microflex tube (Kontes) and evaporated to dryness under a stream of nitrogen. To the dried residue was added 10 μg of 16β-bromoestradiol of Example I dissolved in 10 μl of freshly distilled 2-butanone. The vial was sealed with a Teflon-lined stopper, placed in an oven at 66° to 68° C., and heated for 4 to 6 hours. At the end of this time, 10 μl of 2-butanone was added to ensure against the complete evaporation of solvent and the reaction was continued overnight. The contents of the tube were transferred to a test tube (15 by 100 mm) with 5 ml of methylene chloride. This solution was washed once with 1 ml of 0.1N Na$_2$S$_2$O$_3$ and then with 1 ml of water, after which the organic solvent was dried over anhydrous Na$_2$SO$_4$, filtered, and evaporated under nitrogen.

The residue was then chromatographed on a silica gel column, which cleanly separates the $^{125}$I-labeled estradiol from the starting material as illustrated in FIG. 1. The residue of the methylene chloride extract obtained from the reaction of Na$^{125}$I with 16β-bromoestradiol was dissolved in 0.25 ml of benzene-ethyl acetate (99:1) and chromatographed on a column (8.5 by 1 cm) of thin-layer grade silica gel in the same solvent. The column was eluted under N$_2$ pressure at a flow rate of approximately 60 ml/hour. Fractions of 4 ml were collected. Unreacted 16β-bromoestradiol was detected by high-pressure liquid chromatography, using an ultraviolet detector at 280 nm.

In several experiments the yield of $^{125}$I-labeled estradiol ranged from 25 to 65 percent of the incubated $^{125}$I. The purified radioactive iodinated compound was stored at 0° to 4° C. in a benzene-methanol mixture (95:5). Unlike [$^3$H]estradiol at 100 Ci/mmole, the $^{125}$I-labeled compound is very stable and showed no signs of decomposition after weeks of storage.

EXAMPLE 3

Binding of 16α-[$^{125}$I]iodoestradiol To Rat Uterine Receptor

To deterine whether 16α-[$^{125}$I]iodoestradiol would be recognized by estrogen-responsive tissues, it was injected into castrated female rats with and without diethylstilbestrol (DES); after 6 hours the concentration of radioactivity in the uterus was compared to that in several other tissues.

Female Sprague-Dawley rats (200 to 250 g) were castrated 48 hours before subcutaneous injection of $^{125}$I-labeled estradiol (1×10$^6$ count/min) dissolved in 10 μl of ethanol and 0.2 ml of saline. Twenty minutes before the administration of the iodinated estradiol, one group of rats (N=6) were injected with 5 μg of DES dissolved first in 50 μl of ethanol and then in 0.5 ml of saline. Another group of castrated rats (N=6) were injected with 0.5 ml of 10 percent ethanol in saline before receiving the radioactive steroid. The rats were killed 6 hours later and small pieces of the tissues were weighed and counted. All values are means ± standard deviations. To determine ether extractable radioactivity, the uterus, liver, and thyroid were homogenized in methanol and filtered. The filtrate was evaporated and the resulting residue was partitioned between ether and 0.1N NaHCO$_3$. The ethereal solution was evaporated and counted and the results are tabulated below in Table I.

TABLE I

| Tissue | Radioactivity (count/min per 100 mg of tissue) | | Ether-extractable radioactivity (%) |
|---|---|---|---|
| | Without DES | With DES | |
| Uterus | 313 ± 150** | 73 ± 8 | >90 |
| Liver | 446 ± 184 | 425 ± 105 | 10–15 |
| Kidney | 73 ± 33 | 75 ± 20 | |
| Serum | 69 ± 11 | 68 ± 6 | |
| Lung | 47 ± 23 | 56 ± 11 | |
| Muscle | 33 ± 23 | 18 ± 12 | |
| Heart | 23 ± 5 | 26 ± 7 | |
| Thyroid* | 1839 ± 802 | 2287 ± 805 | 0–1 |

*Radioactivity in the thyroid is for the entire organ.
**Standard deviation

The results of Table I show that the concentration of radioactivity was greater in the uterus than in all other tissues except the liver and thyroid gland. However, the uterus was the only organ in which the uptake of the radioactivity was decreased by DES. This competition for uptake in the uterus by the nonsteroidal estrogen DES demonstrates the specificity of the concentration of the radio activity by this organ. Furthermore, when the amount of ether-soluble radioactivity was compared, the uterus had a much greater concentration of radioactivity than both the liver and the thyroid (Table I).

Several micrograms of 16α-iodoestradiol were added to the ether extract of the uterus and the mixture was submitted to high-pressure liquid chromatography. High pressure liquid chromatography was performed on a 250 by 4.6 mm Lichrosorb Diol column (merck) with methylene chloride at a flow rate of 1 ml/min. In this system 16α-iodoestradiol is eluted in 12 minutes and 16β-bromoestradiol in 8 minutes. Virtually all the radioactivity migrated with the carrier, demonstrating the radioactive material in the uterus was unmetabolized $^{125}$I-labeled estradiol. The radioactivity in the thyroid gland, approximately 2000 count/min, is probably due to the uptake of free iodide arising from the metabolism of $^{125}$I-labeled estradiol in vivo and is equivalent to only 0.2 percent of the injected dose.

EXAMPLE 4

Binding of $^{125}$I-labeled estradiol to rat uterine cytosol

Both $^3$H-labeled and $^{125}$I-labeled estradiol were incubated with cytoplasm from the uteri of rats and the amount of bound steroid was determined as described by Nugent et al., *J. Clin. Endocrinol. Metab.* 26, 1116 (1966) and Korenman, *Methods Enzymol.* 36, 49(1975), which are hereby incorporated by reference. Uteri obtained from rats (200 to 250 g) ovariectomized 24 hours previously were homogenized in four volumes of TED buffer (0.01M tris-HCl, pH 7.4, 2.5 mM EDTA, and 5 mM dithiothreitol) with two to three pulses of 15 seconds each in a Brinkmann Polytron. The homogenate was centrifuged at 4000 g for 10 minutes and the resulting supernatant for 60 minutes at 150,000 g. Portions (100 μl) of the supernatant (cytosol) containing 98 μg of protein were added to the radioactive estrogens ($^{125}$I-labeled estradiol, 112 Ci/mmole; [6,7-$^3$H]estradiol, 45 Ci/mmole) dissolved separately in 150 μl of TED buffer with and without $7 \times 10^{-7}$M DES. Samples were incubated for 4 hours at 0° to 2° C. Free steroid was removed by addition of 250 μl of a suspension of 0.5 percent dextran-coated charcoal. The tubes were mixed and then centrifuged at 5000 μg for 10 minutes. The bound radioactivity remaining in solution was then counted and is tabulated below in Table II.

TABLE II

| | Radioactivity (count/min) | | | |
|---|---|---|---|---|
| Ligand | Added | Bound without DES | Bound with DES | Radioactivity specifically bound (count/min) |
| [16α-$^{125}$I]Iodoestradiol | 69,600 | 42,600 | 3,800 | 38,800 (56 percent) |
| [6,7-$^3$H]Estradiol | 63,600 | 28,900 | 5,800 | 23,100 (36 percent) |

The data in Table II show that a larger percentage of the $^{125}$I-labeled estradiol than of the [$^3$H]estradiol is bound and that there is less nonspecific binding with the iodinated estradiol. Slightly more [$^3$H]estradiol is bound when the difference in specific activities is taken into account.

EXAMPLE 5

In a separate set of experiments the cytoplasmic extracts, incubated with the iodinated and tritiated tracer, were centrifuged on glycerol gradients (as described in Taft et al., *Methods Enzymol.* 36, 156 (1975)) in the presence and absence of 0.4M KCl. The analysis was performed with glycerol rather than the usual sucrose because a more pronounced 8S peak was obtained in the glycerol gradients with both $^3$H- and $^{125}$I-labeled estradiol. Rat uterine cytosol was prepared as described in Example 4. Cytosol was diluted 1:1 with TED buffer (0.1M Tris-HCl, ph 7.4/2.5 mM EDTA/5 mM dithiotreithol) and 0.5 ml of the mixture was incubated for 3 hours at 0° C. with $^{125}$I-labeled estradiol (500,000 count/min; 112 Ci/mole) with and without DES ($7 \times 10^{-7}$M). Separate tubes also contained 0.4M KCl. At the end of the incubation, free steroid was removed by adding the incubation mixture to a tube containing a 5-mg pellet of dextran-coated charcoal. After shaking for 5 to 10 minutes at 0° C., the charcoal was removed by centrifugation. A 200-μl portion of each charcoal-treated cytosol was layered on 3.8 ml of a 15 to 40 percent linear gradient of glycerol prepared in TED buffer or TED buffer containing 0.4M KCl and centrifuged at 50,000 rev/min for 18 hours in a Beckman SE-60 rotor. Fractions of four drops were collected from the bottom of the tube. Control tubes containing cytosol mixed with $^{14}$C-labeled bovine serum albumin (BSA) as a marker were also analyzed. The sedimintation pattern is illustrated in FIG. 2.

Figure 2:
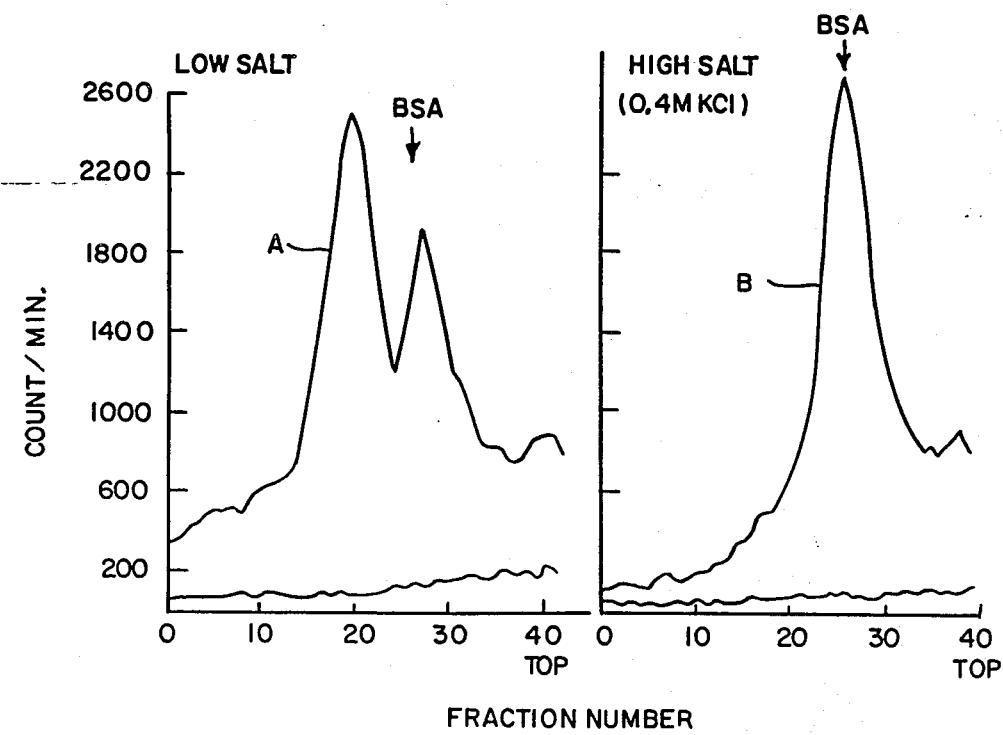
FIG. 2 illustrates the sedimentation pattern of $^{125}I$-$E_2$ in linear glycerol gradients with low salt (Curve A) and high salt (Curve B).

The low-salt 8S form (FIG. 2, Curve A) is totally transformed into the 4S form by 0.4M KCl (FIG. 2, Curve B). The radioactivity bound to both the 8S and 4S forms is almost completely displaced by DES. The glycerol density gradients of the cytoplasmic extracts incubated with [$^3$H]estradiol (not shown) were identical to those incubated with the iodinated tracer with two exceptions: there were less bound radioactivity and more nonspecific binding of [$^3$H]estradiol than of $^{125}$I-labeled estradiol.

EXAMPLE 6

Purified I-E$_2$

After synthesis of the brominated steroid, 16β-bromoestradiol (BR-E$_2$), as in Example 1, 5 mg of it was dissolved in 500 μl of CH$_2$Cl$_2$ and subjected to high-pressure liquid chromatography on a column of Lichrosorb Diol (250×4.6 mm, Merck) which was eluted at 1 ml/min with CH$_2$Cl$_2$. The brominated steroid eluted in a sharp peak in 8 minutes. This purified Br-E$_2$ served as the substrate for a modified halogen exchange procedure.

One to 2 mCi of carrier-free Na$^{125}$I in 5–10 μl of aqueous medium was added to 100 μl of freshly distilled acetonitrile in a 100-μl microflex tube (Kontes) and was taken to dryness under a stream of nitrogen. Because some $^{125}$I is entrained in the vapor, the entire evaporation process was carried out in a hood in an enclosed vessel that had an exit port connected to a charcoal-filled filter. To the dried residue we added 10 μg of bromo-estradiol and 30 μl of freshly distilled 2-butanone. The mixture was stoppered with a Teflon lined cap and heated overnight at 78° C. in a heated block; the next morning the products were extracted and chromatographed on a silica gel column as described in Example 2. Those fractions containing $^{125}$I-E$_2$ were combined, evaporated, dissolved in 250 μl of CH$_2$Cl$_2$, and subjected to high-pressure liquid chromatography as above. The $^{125}$I-E$_2$, which eluted at about 12 ml, was separated cleanly from the Br-E$_2$, which eluted at 8 ml. The mass associated with the tracer was detected at 280 nm and quantified by comparing the area of the UV-absorbing peak with a standard curve produced with known amounts of I-E$_2$.

EXAMPLE 7

Estrogen Receptor Analysis

Fresh calf uteri obtained from a slaughterhouse were brought to the laboratory on ice, immediately trimmed of fat, and cut into small pieces; the pieces were frozen in liquid nitrogen and pulverized. The pulverized frozen tissue was lyophilized, and the desiccated powder was stored under vacuum in sealed vials at −80° C. The uterine powders were usually used within 1 month of pulverization. When needed, the powders were suspended in 0.1M Tris-HCl, pH 7.4/2.5 mM EDTA/5 mM dithiotreithol (TED buffer) at 2.5 mg/ml and homogenized at 0° C. in a Polytron homogenizer with two or three pulses at 15 seconds each. The homogenate was then centrifuged at 150,000×g for 60 minutes and the resulting supernatant (cytosol), containing approximately 1 mg of protein per ml, was used for binding studies on the estrogen receptor.

The binding of $^3H$-$E_2$ and $^{125}I$-$E_2$ to the estrogen receptor was determined by adsorbtion of the free steroid with dextran-coated charcoal. In brief, varying amounts of the radioactive ligands, with or without 0.7 μM diethylstilbestrol (DES), were added in duplicate to 10×75 mm test tubes. After the solvent was removed under a stream of $N_2$, 250 μl of cytosol was added and the samples were incubated at 0°-2° C. overnight. The following morning, 250 μl of a 0.5% suspension of dextran-coated charcoal in TED buffer was added to the tubes which then were mixed and centrifuged at 5000×g for 10 minutes. The supernatant was assayed to determine bound radioactivity.

EXAMPLE 8

Binding of $^3H$-$E_2$ to the Calf Uterine Receptor

We studied binding of I-$E_2$ to the calf uterine estrogen receptor for several purposes. By doing experiments in which unlabeled I-$E_2$ was used to displace a small (subsaturating) constant amount of $^{125}I$-$E_2$ and parallel experiments in which variable amounts of $^{125}I$-$E_2$ were used, we could determine the specific activity of the $^{125}I$-$E_2$. In the same experiment we could ascertain directly the association constant for I-$E_2$ with the receptor. Using the same uterine preparation, we could also compare these values to those obtained with $^3H$-$E_2$.

A saturation analysis of the estrogen receptor from calf uterus was conducted. Calf uterine estrogen receptor was prepared and assayed with increasing concentrations of either $^3H$-$E_2$ or $^{125}I$-$E_2$. Nonspecific binding, specific binding and total binding were determined in parallel incubations containing 0.7 μM DES. It was readily seen that an increase in sensitivity and decrease in counting time can be achieved because of the more efficient detection of $^{125}I$ compared to $^3H$.

A Scatchard analysis of the estrogen receptor from calf uterus was also conducted. The $^{125}I$-$E_2$ experiment was done with a constant amount (61,000 dpm, 83 pM) of the isotopically labeled steroid and increasing concentrations of unlabeled I-$E_2$. The same result was obtained with increasing concentrations of $^{125}I$-$E_2$. For $^3H$-$E_2$: $K_a=6.4\times10^9 M^{-1}$; binding capacity=401 fmol/mg of protein. For I-$E_2$: $K_a=7.1\times10^9 M^{-1}$; binding capacity=411 fmol/mg of protein. The specific activity of the $^{125}I$-$E_2$ used in these experiments, determined from its UV absorbtion on high-pressure liquid chromatography was 1250 Ci/mmol, which was in excellent agreement with the value, 1310 Ci/mmol, determined from binding experiments.

Whereas the ration of the specific activity of the $^{125}I$-$E_2$ to that of the $^3H$-$E_2$ in this experiment was about 30, the ratio of binding capacities is close to 45(122,000 cpm of $^{125}I$-$E_2$ bound compared to 2800 cpm of $^3H$-$E_2$). This apparent discrepancy is accounted for by the difference in counting efficiencies for the two isotopes. The high counting efficiency of $^{125}I$ is one of its important advantages. We stress that the specific activity of the $^{125}I$-$E_2$ was arrived at without reference to the $^3H$-$E_2$ and that the Scatchard plot demonstrates that the number of specific binding sites in uterine cytosol for both compounds is precisely the same. It is also apparent that the dissociation constant (which is based on the slope) for both compounds is the same. Finally, the level of nonspecific binding not only is acceptably low for $^{125}I$-$E_2$ but also is less than that of the $^3H$-labeled hormone.

EXAMPLE 9

Estrogen Receptor Specificity

In order to be sure that both $^{125}I$-$E_2$ and $^3H$-$E_2$ bound with similar specificities, experiments were undertaken in which a series of compounds were allowed to compete with the two differently labeled estrogens for sites on the estrogen receptor.

Several compounds, at the two indicated concentrations, were allowed to compete with both labeled steroids for sites in calf uterine cytosol. Incubations were overnight at 4° C., and bound and free steroids were separated with dextran-coated charcoal. The concentrations were: $^3H$-$E_2$, $1.6\times10^5$ dpm/ml (0.74 nM); $^{125}I$-$E_2$, $6.0\times10^5$ dpm/ml (0.22 nM). $B_0$, dpm specifically bound when only the radioactive compound was present; B, dpm bound in the presence of the indicated concentration of competitor. % $B_0=40\%$ for $^{125}I$-$E_2$ and 11% for $^3H$-$E_2$. Nonspecific binding was determined by parallel incubations in the presence of 70 nM DES as in Example 7. The results are shown in Table III.

TABLE III

| COMPETITION FOR THE ESTROGEN RECEPTOR | | | | |
|---|---|---|---|---|
| | $B/B_0 \times 10^2$ | | | |
| | $^{125}I$-$E_2$ | | $^3H$-$E_2$ | |
| Compound | 0.5 nM | 5 nM | 0.5 nM | 5.0 nM |
| I-$E_2$ | 35 | 2 | 69 | 12 |
| $E_2$ | 34 | 1 | 66 | 30 |
| Estrone | 67 | 17 | 99 | 50 |
| Estriol | 70 | 20 | 92 | 47 |
| DES | 32 | 0 | 60 | 0 |
| Testosterone | 93 | 93 | 97 | 95 |
| 5α-Dihydrotestosterone | 100 | 96 | 99 | 95 |
| Dehydroisoandrosterone | 104 | 107 | 98 | 108 |
| Progesterone | 98 | 102 | 97 | 102 |
| 17α-Hydroxyprogesterone | 106 | 106 | 93 | 91 |
| Corticosterone | 100 | 93 | 103 | 97 |
| Cortisol | 94 | 103 | 105 | 100 |
| Dexamethasone | 100 | 98 | 100 | 100 |

Only compounds with estrogenic activity were active in displacing $E_2$ labeled with either isotope; none of the $C_{19}$ or $C_{21}$ steroids competed. Because of the difference in concentration between $^{125}I$-$E_2$ and $^3H$-$E_2$ and the consequent difference in initial binding (40 and 11%, respectively), precise quantitative comparison between the two compounds is not possible; it is apparent, however, that, regardless of which radioactive ligand was used, $E_2$ and I-$E_2$ were about equipotent in competing for the estrogen receptor. This is consistant with, and confirms, the independently arrived at data which show that the binding constant for the two isotopically labeled estrogens are identical.

EXAMPLE 10

Radioimmunoassay

Antisteroid antisera were produced in rabbits immunized with steroid-bovine serum albumin conjugates. Antibodies against estradiol 17-hemisuccinate-albumin, estradiol-6-carboxymethyloxime-albumin, and 3-carboxymethyl ether of $E_2$ conjugated to albumin were prepared by standard technique well known to those skilled in the art.

Varying amounts of $E_2$ dissolved in methanol were added to test tubes and evaporated to dryness. The residues were dissolved in 100 µl of antiserum that had been diluted in 0.1M phosphate, pH 7.0/0.015M sodium azide/0.15M NaCl/0.1% gelatin (PBS buffer). After the mixture had incubated at room temperature for 30 minutes, 100 µl of PBS buffer containing 10,000 cpm of either $^{125}I$-$E_2$ or $^3H$-$E_2$ was added to the tubes and the incubation was continued for 1 hour at room temperature and then for 30 minutes at 4° C. Upon completion of the incubation, 100 µl of 0.5% gelatin in PBS buffer was added, followed by 1 ml of PBS buffer containing 2.5 mg of dextran-coated charcoal. The mixture was agitated in a vortex mixer and, after 10 minutes at 4° C., it was centrifuged at 5000×g for 10 minutes at 4° C. Aliquots (0.9 ml) were assayed for radioactivity.

Both $^3H$-$E_2$ (43 Ci/mmol) and $^{125}I$-$E_2$ (1300 Ci/mmol) were incubated with various dilutions of antisera produced against bovine serum albumin complexes with $E_2$-17-hemisuccinate, $E_2$-6-carboxymethyloxime, and $E_2$-3-carboxymethyl ether; displacement of the bound tracer by picogram amounts of $E_2$ was measured. Whereas both the $^3H$-$E_2$ and $^{125}I$-$E_2$ bound to all three antisera, the importance of the great difference in the specific activities became apparent at very high dilutions of the antibodies. These antisera were capable of binding sizeable amounts of the iodinated steroid at dilutions that bound barely measurable quantities of $^3H$-$E_2$. The data also indicate that very sensitive radioimmunoassays could be developed with all three antisera. In fact, with anti-$E_2$-6-carboxymethyloxime-albumin, almost 50% of the tracer was displaced from the antibody with only 1 pg of $E_2$.

EXAMPLE 11

I-$E_2$ Binding To Human Mammary Tumors

Extrogen receptor human mammary tumors were kept frozen in dry ice in a pulverized form. The cytosol was prepared and assayed as described in Example 7 for the calf uteri with the exception that 50 mg of tumor tissue was homogenized in 1 ml of TED buffer. The final concentration of cytosolic protein used in the assay was 1.5 mg/ml.

A pool of two different estrogen receptor-positive mammary tumors was studied. Each was assayed at a protein concentration of 1.5 mg/ml with eight different concentrations of $^3H$-$E_2$ and $^{125}I$-$E_2$. Using $^{125}I$-$E_2$, we found the receptor concentration to be 24 fmol/mg of protein for the first pool (no. 124) and 72 fmol/mg for the second (no. 126). With $^3H$-$E_2$, the respective concentrations were 36 and 64 fmol/mg of protein.

EXAMPLE 12

Estrogen Bioassay

Estrogenic potency was assayed in 21-day-old female rats. Groups of six rats received daily subcutaneous injections of various doses of $E_2$, I-$E_2$, or sesame oil (control) for 3 days. On the fourth day, the uteri were removed, trimmed, blotted, and weighed.

The results show that I-$E_2$ is estrogenic in vivo, albeit not as potent as $E_2$ itself. This difference in potency, can be explained either by differences in the peripheral metabolism of the two compounds or by differences in events that occur after binding to the cytosolic receptor has taken place. At this time we believe the former explanation to be correct because the two estrogens are equipotent in vitro in inducing growth of an estrogen-dependent human breast tumor cell line (MCF-7).

EXAMPLE 13

External Localization Of $^{131}I$-$E_2$

The tracer $^{131}I$-$E_2$ was synthesized as described in Example 6 with the exception that Na $^{131}I$ was used for the exchange. The subject, a squirrel monkey (Saimari Sciureus), weighing 1.5 kilograms, was ovariectomized 2 weeks before the start of the experiment and an estradiol containing Silastic implant was placed subcutaneously in her back. The implant was removed 24 hours before the intravenous injection of 200 µCi of the tracer dissolved in saline. The animal was scanned constantly with a pin-hole collimator and uptake of the tracer in the liver could be seen immediately. Within 1 to 2 hours radioactivity could be detected in the suprapubic region, but when the bladder was aspirated and washed, 3.8 µCi of radioactivity was found in the urine. At this point the amount of radioactivity detected by the scanner was greatly reduced but another region of radioactivity immediately adjacent to the bladder then became apparent. The uterus was then imaged with an Anger Camera. These results indicate that $^{125}I$-$E_2$ or $^{131}I$-$E_2$ can be useful as radioimaging agents for the detection of estrogen receptor containing cancers.

The invention has been described in detail including the preferred embodiments thereof. However, it will be appreciated that modification within the spirit and scope of this invention may be made by those skilled in the art. For instance, as aforesaid, one skilled in the art can readily apply the teachings disclosed herein to any 3,17β-dihydroxy steroidal estrogen such as, for example, dihydroxy equilin, dihydroxy equilenin, and the like.

I claim:

1. A 16α-halo-3,17β-dihydroxy steroidal estrogen wherein the halogen is radioactive.

2. The compound of claim 1 wherein said halo substituent is iodo.

3. The compound of claim 2 wherein said radioiodide is $^{123}I$, $^{125}I$ or $^{131}I$.

4. The compound of claim 1 wherein said estrogen is selected from estradiol, 17β-dihydro equilin or 17β-dihydro equilenin.

5. 16α-Iodoestra-1,3,5(10)-triene-3,17β-diol.

6. 16α-Haloestra-1,3,5(10)-triene-3,17β-diol wherein said halo substituent is radioactive.

7. The compound of claim 6 wherein said halo substituent is $^{123}I$.

8. The compound of claim 7 wherein said halo substituent is a radioiodide.

9. The compound of claim 8 wherein said radioiodide is $^{123}I$, $^{125}I$ or $^{131}I$.

10. A method for preparing a radiohalogenated 16α-halo-3,17β-dihydroxy steroidal estrogen comprising reacting the corresponding 16β-bromo-3,17β-dihydroxy steroidal estrogen with a radiohalide wherein said 16β-bromo-3,17β-dihydroxy steroidal estrogen is present in an amount of at least about 10 times the number of moles of radiohalide, and separating the radioactive 16α-halo-3,17β-dihydroxy steroidal estrogen from the reaction mixture.

11. A method of claim 10 wherein said radiohalide is a radioiodide.

12. The method of claim 11 wherein said radioiodide is $^{123}$I, $^{125}$I or $^{131}$I and said 16β-bromo-3,17β-dihydroxy steroidal estrogen is present in an amount of about 30 times the number of moles of radioiodide.

13. A radiopharmaceutical preparation comprising radiohalogenated 16-halo-3,17β-dihydroxy steroidal estrogen in a pharmaceutically acceptable carrier.

14. The preparation of claim 13 wherein said radiolabelled estrogen is a radioiodinated estrogen.

15. The preparation of claim 13 wherein said steroidal estrogen is a 16α-radioiodoestra-1,3,5(10)-triene-3,17β-diol.

16. A method for in vivo localization of tissue containing estrogen receptor activity comprising intravenously or lymphatically injecting a higher animal with a radiopharamaceutical preparation as described in claim 13, 14 or 15 and visualizing said tissue with radioscintigraphic imaging equipment.

17. The radiopharmaceutical preparation of claim 13, 14 or 15 wherein said radiolabelled estrogen is present in a therapeutically effective tumor treating amount.

18. The compound of claim 1 wherein the specific activity is at least 1000 Ci/mmol.

* * * * *